United States Patent [19]
Tuffery

[11] Patent Number: 6,116,249

[45] Date of Patent: Sep. 12, 2000

[54] METHOD AND APPARATUS FOR EXTRACTING PARTICLES PRODUCED BY THE TREATING OF HUMAN OR ANIMAL NAILS

[76] Inventor: Donald Edward Tuffery, 1 Furze Croft, New Milton, Hampshire BH25 6NH, United Kingdom

[21] Appl. No.: 09/043,281

[22] PCT Filed: Jul. 11, 1997

[86] PCT No.: PCT/GB97/01883

§ 371 Date: Sep. 29, 1998

§ 102(e) Date: Sep. 29, 1998

[87] PCT Pub. No.: WO98/02060

PCT Pub. Date: Jan. 22, 1998

[30] Foreign Application Priority Data

Jul. 16, 1996 [GB] United Kingdom .................... 9614914

[51] Int. Cl.[7] .................................................. A45D 24/00
[52] U.S. Cl. ........................... 132/200; 132/73; 132/73.5; 132/286; 55/473; 454/57; 454/63; 454/66
[58] Field of Search ............................ 132/73, 73.5, 286, 132/200; 55/385.1, 467, 473; 454/57, 63, 66

[56] References Cited

U.S. PATENT DOCUMENTS

| | | | |
|---|---|---|---|
| D. 360,873 | 8/1995 | Starec et al. ............................ | D13/143 |
| 3,880,061 | 4/1975 | Hensiek et al. ........................... | 454/66 |
| 4,280,519 | 7/1981 | Chapman ................................ | 132/73.5 |
| 4,647,295 | 3/1987 | Christ ...................................... | 55/473 |
| 4,852,468 | 8/1989 | Harris ...................................... | 132/73 |
| 5,139,036 | 8/1992 | Pickard ................................... | 132/73.5 |
| 5,139,546 | 8/1992 | Novobilski .............................. | 55/316 |
| 5,316,560 | 5/1994 | Krome-schmidt et al. ............... | 55/473 |
| 5,336,128 | 8/1994 | Birdsong ................................. | 454/56 |
| 5,366,275 | 11/1994 | Sulzer ................................. | 297/347.19 |
| 5,464,029 | 11/1995 | Rentz .................................... | 132/73.5 |
| 5,787,903 | 8/1998 | Blackshear .............................. | 132/73 |

FOREIGN PATENT DOCUMENTS

| | | | |
|---|---|---|---|
| 8512617 | 9/1985 | Germany ............................... | 132/73.5 |
| 334209 | 8/1930 | United Kingdom .................. | 132/73.5 |
| 2 315 208 | 1/1998 | United Kingdom . | |

*Primary Examiner*—Gene Manoene
*Assistant Examiner*—Pedro Philogene
*Attorney, Agent, or Firm*—Skjerven, Morrill, MacPherson, Franklin & Friel LLP; Alan H. MacPherson; Hugh H. Matsubayashi

[57] ABSTRACT

Method and apparatus for removing dust produced by the treating of human or animal nails. An air current produced by a fan is directed through an adjustable conduit towards the nails being treated. A funnel attached to a second adjustable conduit leading to a filter is positioned beyond the nails so that dust particles are entrained by the air current and carried into the funnel and to the filter. The fan is of sufficient power to cause very fine dust particles to be removed.

20 Claims, 3 Drawing Sheets

METHOD AND APPARATUS FOR EXTRACTING PARTICLES PRODUCED BY THE TREATING OF HUMAN OR ANIMAL NAILS

The present invention relates to removal of dust particles produced by the treating of human or animal nails.

INTRODUCTION

A common foot related problem requiring treatment by a chiropodist is thickened nails. One method of treating this condition is to remove a part of the nail using a grinding wheel. Chiropodists often have to visit the homes of patients to perform this treatment as it might be too painful for the patient to walk to a surgery. This means that the chiropodist must carry equipment with them to the patient's home.

A considerable amount of dust is produced whilst performing the nail grinding. For hygiene purposes the resulting dust needs to be cleaned. This can be difficult if the treatment is not performed at the surgery, for example the dust might need to be removed from a carpet on the floor of a patient's home. A potentially more serious problem is the very fine dust particles which are produced by grinding nails. Dust particles of up to 12.0 microns in size can penetrate the respiratory tract. This can cause lung problems, particularly for a chiropodist, who is exposed to such particles frequently over a long period of time. People with respiratory problems are also especially prone to these undesirable effects.

The wearing of a surgical mask will help prevent the inhalation of dust particles. However, it is more effective to prevent dust particles from entering the surrounding air. Known dust extraction devices for use in the treatment of nails rely on suction to extract dust particles. These techniques are not very effective for dealing with very fine dust particles. The suction device has to be positioned very close to the nail being treated in order to remove particles effectively. This requirement can restrict the chiropodist's workspace for performing the grinding and also means that the patient may have to move their foot several times during the treatment. The resulting apparatus may also be large and heavy and therefore not feasible for carrying for use during home visits. Some grinding wheels are fitted with dust extraction systems, but these are expensive and again rely on suction so they do not effectively deal with very small dust particles.

It is an object of the present invention to provide a relatively low cost portable device which can extract very small dust particles from the air whist overcoming the limitation of having to position a suction device directly by the nails being treated.

SUMMARY OF THE INVENTION

According to a first aspect of the present invention there is provided an apparatus for extracting particles produced by the treating of human or animal nails, comprising: support means; means for generating an air current; and dust extraction means, wherein said support means is positioned between said air current generating means and said dust extraction means.

According to a second aspect of the invention there is provided a method for removing dust by treating nails comprising steps of:
 generating an air current;
 placing nails being treated in the air current; and
 positioning a dust extraction means such that the air current carrying the dust enters the dust extraction means.

According to a third aspect of the present invention there is provided a kit of parts for use in treating nails, comprising:
 grinding apparatus;
 a light source;
 a socket set; and
 apparatus for extracting particles produced by the treating of human or animal nails.

DETAILED DESCRIPTION OF THE PREFERRED EMBODIMENTS

The invention will now be described by way of example only with reference to the previously identified drawings.

Figure 1:
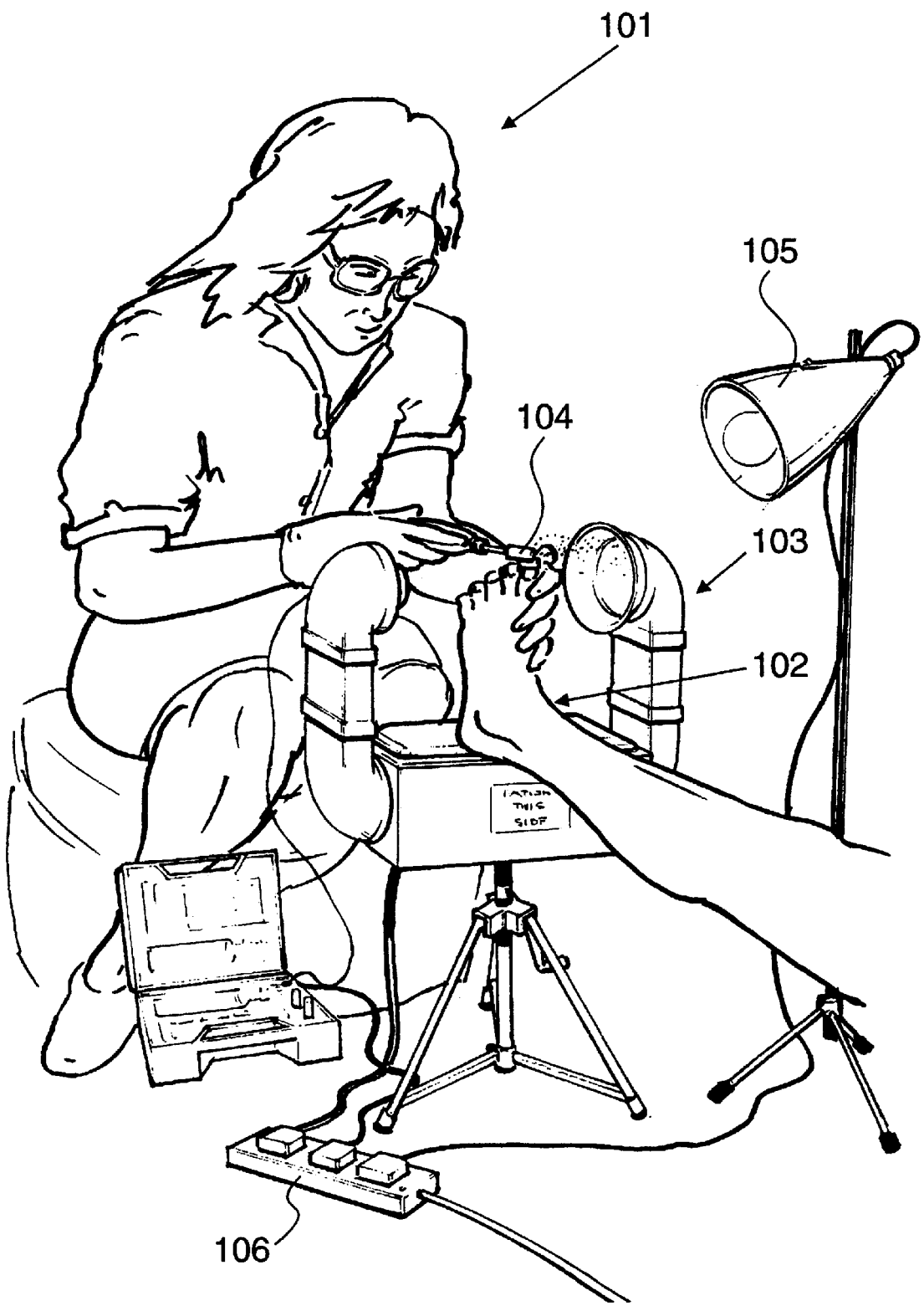
FIG. 1 illustrates an embodiment of the particle extraction device in use.

FIG. 1 illustrates a chiropodist 101 performing nail grinding treatment on a patient. The patient's foot 102 is shown resting on an embodiment of the present invention, portable device 103. The chiropodist uses a grinding wheel tool 104 to perform the treatment. Dust produced by using the grinding wheels on the patient's nails is intended to be removed from the surrounding air by the device 103.

It is the inventor's intention that the device 103 will be marketed as part of a portable chiropody kit. In addition to the device 103, the kit will comprise the grinding wheel tool 104 and a high power light 105 to illuminate the patient's foot. The three components 103, 104 and 105 can be plugged into a multi-socket electrical extension 106, also included in the kit.

Figure 2:
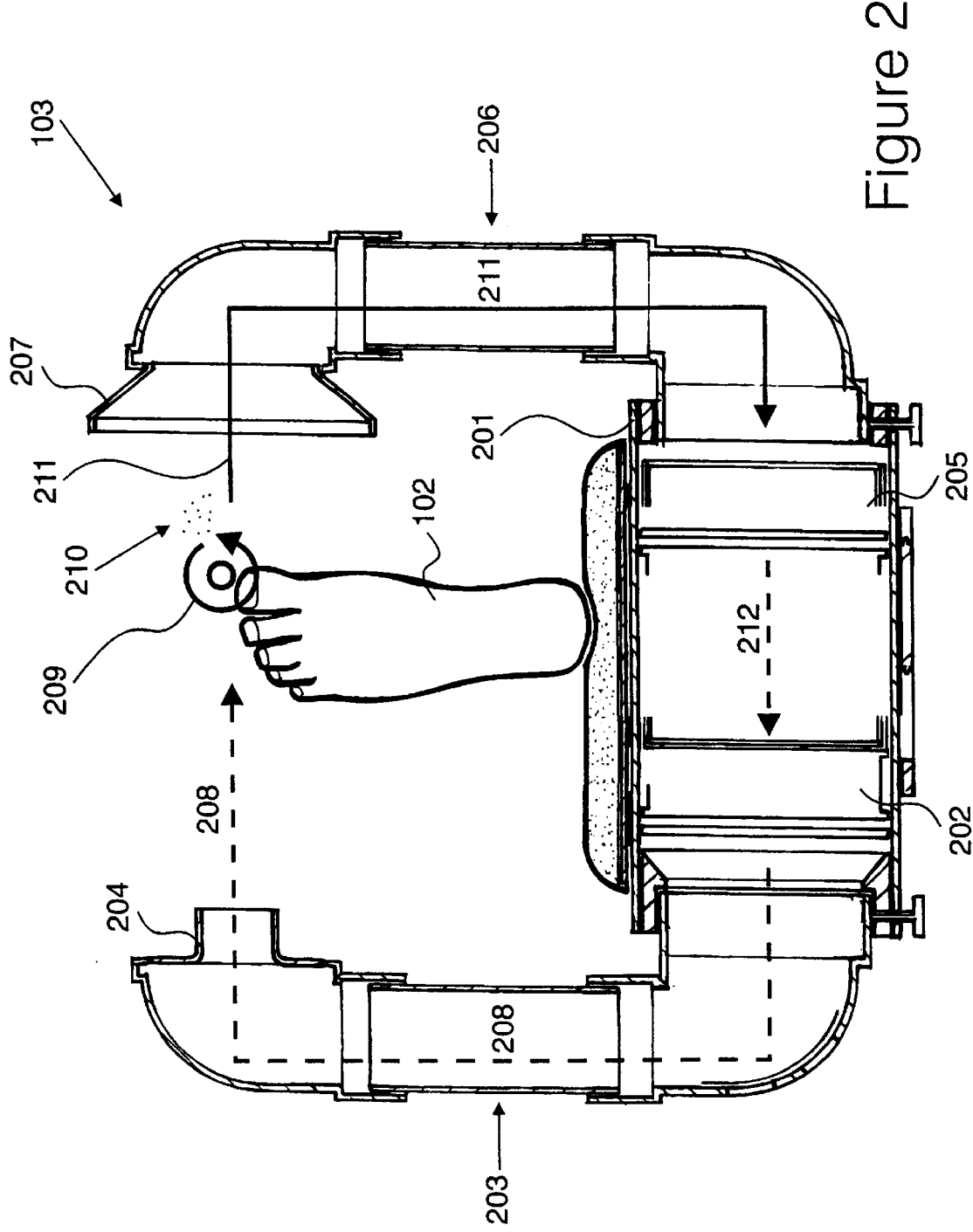
FIG. 2 illustrates a cross-section through the particle extraction device identified in FIG. 1.

FIG. 2 of the accompanying drawings illustrates a cross-section through the device 103 with a patient's foot 102 resting on it. The device 103 comprises a support block 201, which houses a fan 202 and a filter 205, as well as functioning as a footstool for the patient. The fan produces a current of air shown by arrow 208. (From the patient's point of view shown in FIG. 2). The fan 202 is a coaxial extrusion fan with a power which provides a flow rate of at least 138.2 cubic feet per minute. This flow rate is required to entrain very fine dust particles in the air current produced. The fan used in the preferred embodiment is available from RS Components, England from their 1997 catalogue, page 2-1408, stock number 498-081. The air current is blown through a blower arm 203 and exits the blower arm through a nozzle 204. The air current passes over the top of a patient's from where dust 210 is produced by the grinding of nails. The grinding wheel 104 has a grinding member which rotates in an anti-clockwise direction (from the patient's point of view), shown by rotary arrow 209. This means that dust particles produced by the grinding treatment are propelled in the same direction as the air current emerging from nozzle 204. Device 103 is most effective when the direction of the air current and propulsion of dust produced by grinding are coincident, so a sign may be attached to support block 201 in order to help ensure that chiropodist and patient are positioned on the correct sides of the device to achieve this effect.

The dust particles 210 are entrained by the air current and carried towards a funnel 207. The funnel 207 is connected to a receiver arm 206 of the device. At the receiver arm end of the device, the fan 202 produces a suction effect which draws the particle-laden air current in towards the back of the fan. The particle-laden air travels down the receiver arm in the direction of arrow 211 and is led to filter 205. The filter 205 comprises a cardboard case, sized to fit inside case 201, with open ends to form a frame for a filter membrane. The filter membrane is louvered to increase its surface area in order to prevent particles greater than approximately 0.1 microns in size penetrating through it. Filters of this kind are available from 3M, Minnesota, U.S.A. The resulting filtered air current 212 passes into fan 202 and is blown up the blower arm. The filter is configured to trap very fine dust particles, in particular those which can lead to lung problems.

Figure 3:
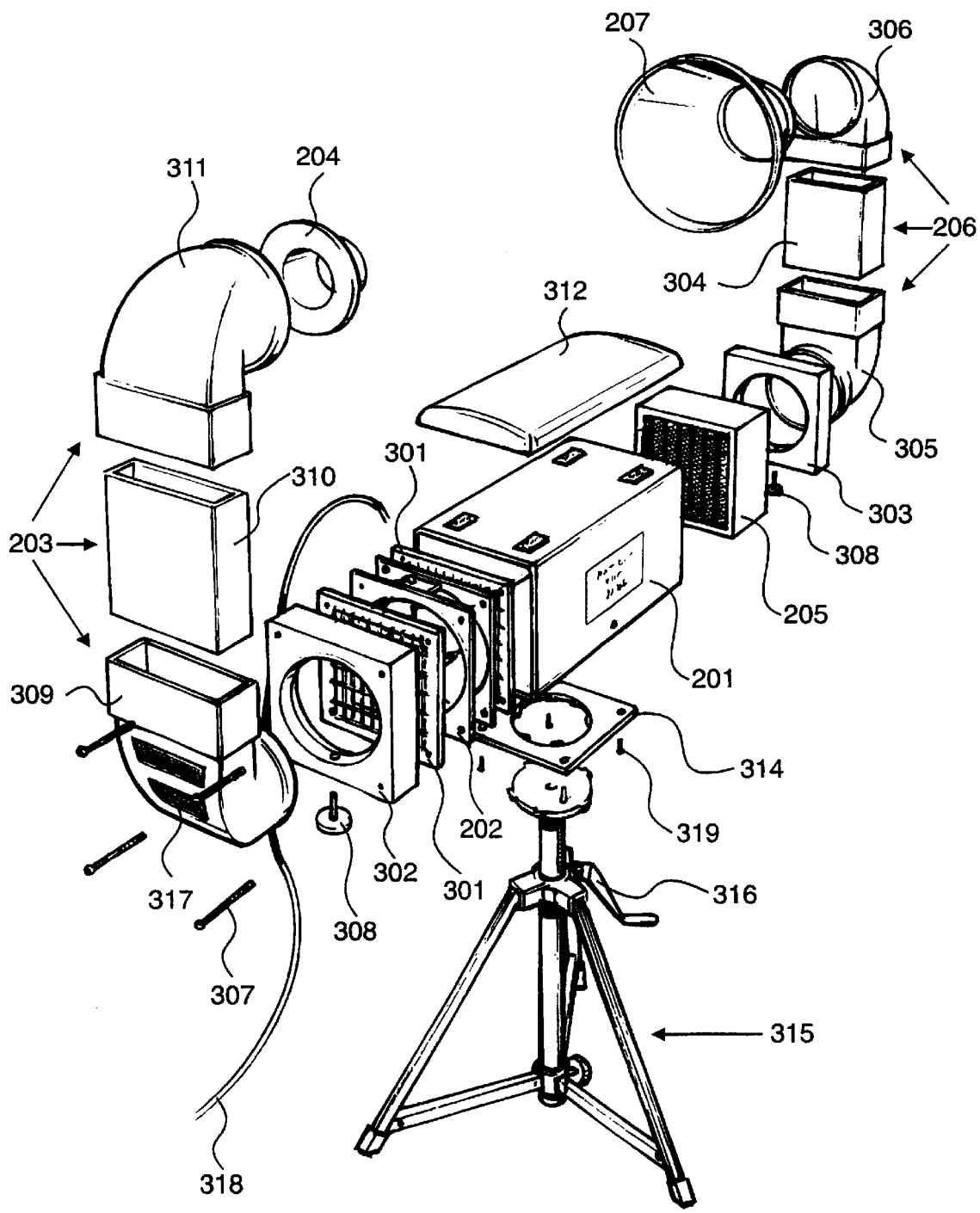
FIG. 3 illustrates an exploded respective view of the particle extraction device shown in FIGS. 1 and 2.

FIG. 3 of the accompanying drawings illustrates an exploded perspective view of the dust extraction device 103. The support block 201 is a substantially rectangular box-shaped plastic extrusion which also acts as a case for some of the device's components. The fan 202 is housed inside the support block near one end. The fan has two grilles 301, one attached to either side of the fan in order to prevent objects entering and coming into contact with the fan's blades. A power lead 318 supplies electricity to the fan.

A plastic moulded end piece 302, substantially square-shaped and substantially similar in size to the square end of support block/case 201, is fitted to the end of the support block nearest the fan and grilles. The end piece 302 has a circular orifice in its centre. The filter 205 is also housed inside the support block 201 at the opposite end to the fan. A plastic moulding 303 (substantially similar to plastic moulding 302) is push-fitted to the other end of the support block, near the filter 205. End piece 303 can thus be easily removed to clean or replace the filter. The end moulding 302, the fan grilles 301 and the extrusion fan 202 each have four threaded holes, one in each corner. The components 301, 302 and 202 are held together by four "secret"-headed tamper-proof screws 307 threaded through their four holes.

The blower arm 203 is attached to end moulding 302 The blower arm consists of three moulded plastic components 309, 310 and 311. A plastic elbow 309 is inserted into the circular orifice in end moulding 302. The elbow 309 is a substantially perpendicular L-shaped hollow plastic moulding with a circular protrusion on one side and a rectangular orifice in its upper surface. The elbow 309 fits into the circular orifice of the end moulding 302 so that the air current produced by the fan will be directed in an upward direction through plastic elbow's 309 upper rectangular orifice.

The surface of elbow 309 may have one or more holes 317 arranged to reduce the efficiency of blower arm 203 relative to receiver arm 206. This means that the suction effect at the funnel 207, attached to receiver arm 206, is more effective for drawing in dust particles. The hole(s) 317 may be covered by a gauze to prevent dust particles escaping. A rectangular plastic tube 310 is fitted on the top end of elbow 309. Another plastic elbow 311 (substantially similar to elbow 209 but having no surface hole(s)) is fitted on to the top of hollow tube 310. A disc-mounted plastic moulded nozzle 204 is fitted into the circular orifice of elbow 311. The elbow 311 can slide vertically on the tube 310 allowing the height of the nozzle to be adjusted. The hollow tube 310 fits inside the rectangular orifices of elbows 309 and 311 so that the air current is directed up through components 309, 310 and 311 which form the blower arm 203. The blower arm 203 acts as a conduit for the air current produced by fan 202 so that the air current exits through nozzle 204 and is directed across the top of support block 201 in the opposite direction to the air current that the fan produces.

Another plastic elbow 305 (substantially similar to elbow 309 but with no surface hole(s)) is fitted to the end moulding 303 closest to the fan. This plastic elbow 305 forms a base part of receiver arm 206. A rectangular plastic tube 304, substantially similar to plastic tube 310, is inserted into the rectangular orifice of plastic elbow 305. A plastic elbow 306 (substantially similar to elbow 311) is inserted onto the top of hollow tube 304. A rounded plastic moulded funnel 207 is fitted into the circular orifice of elbow 306. The funnel 207, elbows 306 and 305 and plastic tube 304 form the receiver arm 206 of the device which acts as a conduit to lead the particle-laden air current down and back into the support block 201 filter 205 and then by recycled by fan 202. Elbow 306 can slide on tube 304 allowing the height of the funnel 205 to be adjusted.

The receiver arm 206 and the blower arm 203 can also be rotated. The circular protrusion of plastic elbow 305 can be rotated within the circular orifice of end moulding 303. End moulding 302 has a threaded brass insert leading from the bottom base of the moulding in a substantially vertical direction to the bottom of its circular orifice. A large headed captive locking screw 308 is fitted through the threaded orifice in end moulding 303. When the screw 308 is tightened it locks the plastic elbow 305 in position. The screw 307 can be loosened and re-tightened in order to adjust and fix the rotation of the receiver arm 206. The end moulding 302 located on the other end of the support block 201 also has a similar threaded brass insert to end moulding 303. A substantially identical large headed captive locking screw 308 is used to adjust the rotation of blower arm 203 in a substantially similar manner to the method described above for receiver arm 206.

A foam cushion 312 with a PVC covering is placed on the upper surface of the support block 201 for the comfort of the patient. The cushion 312 is attached to the support block by means of four Velcro tabs 313. The PVC covering means that the removable cushion is easily cleaned.

The support block 201 and all attached components are mounted on a stand 315. In the preferred embodiment this is a tripod stand with adjustable height and folding legs. A square-shaped plastic moulding 314 with a circular hole designed to fit the top of tripod 315 is fitted to the bottom of support block 201. The plastic moulding 314 has six orifices around the inner circumference of its circular hole into which nibs on the top of tripod stand 315 can fit. The plastic moulding 314 is attached to the support block using four screws 319 threaded through four holes in the corners of the moulding 314 into corresponding holes in the support block's lower surface. The height of the tripod stand can be adjusted by rotating a winding mechanism 316 so that the patient's foot/leg is held on the cushion 312 in a comfortable position.

I claim:

1. Apparatus for extracting particles produced by the treating of human or animal nails, comprising:

a support conduit having an outer surface forming a support for an appendage of said human or animal from which said nails extend, said support conduit defining a first opening and a second opening opposite said first opening;

a fan for generating an air current within said support conduit;

a blower conduit connected to said first opening of said support conduit, said blower conduit directing the air current across said outer surface of said support conduit;

a receiver conduit connected to said second opening of said support conduit, said receiver conduit receiving the air current from said blower conduit; and a filter for extracting particles entrained in the air current, said filter located in one of said support conduit, said blower conduit, and said receiver conduit;

wherein said fan is located in one of said support conduit, said blower conduit, and said receiver conduit.

2. Apparatus according to claim 1, wherein said blower conduit and said receiver conduit are of an adjustable length.

3. Apparatus according to claim 1, wherein said blower conduit defines a nozzle at an end distal from said first opening of said support conduit.

4. Apparatus according to claim 1, wherein said receiver conduit defines a round funnel at an end distal from said second opening of said support conduit.

5. Apparatus according to claim 1, further comprising a stand on which said support conduit is mounted.

6. Apparatus according to claim 5, wherein said stand is a tripod with adjustable height.

7. Apparatus according to claim 1, wherein said blower conduit and said receiver conduit are rotatable.

8. Apparatus according to claim 1, further comprising a removable cushion attached to said outer surface of said support conduit.

9. Apparatus according to claim 1, wherein said fan is a coaxial extrusion fan producing a flow rate of at least 138.2 cubic feet per minute.

10. Apparatus according to claim 1, wherein said filter is configured to prevent penetration of particles greater than approximately 0.1 microns in size.

11. Apparatus according to claim 1, further comprising one or more safety grilles attached to said fan.

12. Apparatus according to claim 1, wherein said air current entering said filter is recycled.

13. Apparatus according to claim 1, wherein said blower conduit defines one or more through holes in its walls.

14. Apparatus according to claim 3, wherein said through holes are covered by gauze.

15. Apparatus according to claim 1, further comprising:

a grinding apparatus positioned within the air current between the blower conduit and the receiver conduit;

a light source located for illuminating said grinding apparatus and said appendage; and a multi-socket electrical extension electrically connected to said grinding apparatus, said light source, and said means for generating air current.

16. Apparatus according to claim 1, wherein said fan and said filter are located in said support conduit.

17. Apparatus for extracting particles produced by the treating of human or animal nails, comprising:

a support for an appendage of the human or animal from which said nails extend;

a first conduit having an adjustable length;

a fan in communication with said first conduit;

a second conduit having an adjustable length;

a filter in communication with said second conduit;

wherein said support is positioned between said first and second conduits and air passes from said first conduit into said second conduit.

18. Apparatus according to claim 17, wherein said support defines a conduit for passing air from said second conduit to said first conduit.

19. A method for removing dust produced by treating nails, comprising steps of:

generating an air current within a conduit;

supporting an appendage from which said nails extend with said conduit;

directing said air current across said nails using a blower conduit communicated with a first end of said conduit;

receiving said air current with a receiver conduit communicated with a second end of said conduit distal from said first end;

directing said received air current with said receiver conduit into said second end of said conduit;

removing said dust entrained within said received air current; and recycling said air current to be repeatedly directed across said nails.

20. Method acording to claim 19, further comprising adjusting a length of said blower conduit and a length of said receiver conduit to optimize said directing of said air current across said nails.

* * * * *